(12) United States Patent
Forssell

(10) Patent No.: US 7,146,989 B2
(45) Date of Patent: Dec. 12, 2006

(54) DENTAL FLOSS HOLDER

(76) Inventor: Erik Forssell, Klöverfors 47, Kåge, SE-934 95 Kåge (SE)

( * ) Notice: Subject to any disclaimer, the term of this patent is extended or adjusted under 35 U.S.C. 154(b) by 442 days.

(21) Appl. No.: 10/399,348

(22) PCT Filed: Oct. 16, 2001

(86) PCT No.: PCT/SE01/02252

§ 371 (c)(1), (2), (4) Date: Apr. 16, 2003

(87) PCT Pub. No.: WO02/32341

PCT Pub. Date: Apr. 25, 2002

(65) Prior Publication Data

US 2004/0094182 A1 May 20, 2004

(30) Foreign Application Priority Data

Oct. 17, 2000 (SE) ................................... 0003736

(51) Int. Cl.
*A61C 15/00* (2006.01)

(52) U.S. Cl. ...................................... 132/326

(58) Field of Classification Search ......... 132/321–327
See application file for complete search history.

(56) References Cited

U.S. PATENT DOCUMENTS

| | | | |
|---|---|---|---|
| 3,892,249 A | 7/1975 | Jones et al. | |
| 4,192,330 A | 3/1980 | Johnson | |
| 5,170,809 A | 12/1992 | Imai et al. | |
| 5,483,982 A | * 1/1996 | Bennett et al. | ............. 132/323 |
| 5,579,786 A | 12/1996 | Wolk et al. | |
| 5,738,124 A | * 4/1998 | Cervato | ...................... 132/323 |

* cited by examiner

*Primary Examiner*—Todd E. Manahan
(74) *Attorney, Agent, or Firm*—Dilworth & Barrese LLP.

(57) ABSTRACT

A dental floss holder comprises a handle (11) and a cartridge (15, 40, 41, 42). The cartridge is U-formed and has a dental floss (20) fastened between its two legs (17, 18). The base (16) of the cartridge is somewhat bow-formed and arranged to be pushed into a straight groove (19) in the handle, and the dental floss is then automatically tensioned because the mounting forces the legs apart.

18 Claims, 3 Drawing Sheets

DENTAL FLOSS HOLDER

TECHNICAL FIELD

This invention relates to a dental floss holder comprising a handle add a cartridge with a base, two legs and a dental floss suspended between the two legs.

BACKGROUND OF THE INVENTION

U.S. Pat. No. 5,579,786-A, U.S. Pat. No. 5,170,809-A and U.S. Pat. No. 5,246,021-A describe dental floss holders. The dental floss holders in these publications do not describe any tensioning of the dental floss. U.S. Pat. No. 5,170,809-A describes a handle with a small bow, the depth of the bow from the handle is the same as the length of the legs. This handle does not consider the corner of the mouth and is therefore not convenient for cleaning the teeth at the back of the mouth. U.S. Pat. No. 3,892,249-A describes a dental floss cartridge in which the dental floss will be tensioned somewhat when the dental floss cartridge is being mounted. The handle in FIG. 12 has a bow, but the bow is not in the plane of the legs. The handle is therefore not convenient for cleaning the teeth at the back of the mouth, except mounting the cartridge in reverse direction. The bow is small and does not consider the corner of the mouth and is therefore not convenient for cleaning the teeth at the back of the mouth. In this design the dental floss is not in line with the handgrip portion.

OBJECT OF INVENTION AND BRIEF DESCRIPTION OF THE INVENTION

It is an object of the invention to provide a dental floss holder which is tiny and convenient to use and in which the dental floss will have a strong tension when used notwithstanding that the cartridge for the dental floss is tiny and inexpensive, easy to mount to the handle and to dismount from the handle. To this end, co-operating means are arranged between the fastening portion of the cartridge and a mounting portion of the handle for receiving the fastening portion and to bend the cartridge base in the plane of the legs in response to the fastening portion being mounted to the handle, thereby to stress the legs away from each other and to tension the dental floss.

The invention is defined by the claims.

DESCRIPTION OF THE EXAMPLES OF THE INVENTION SHOWN IN THE DRAWINGS

Figure 1:
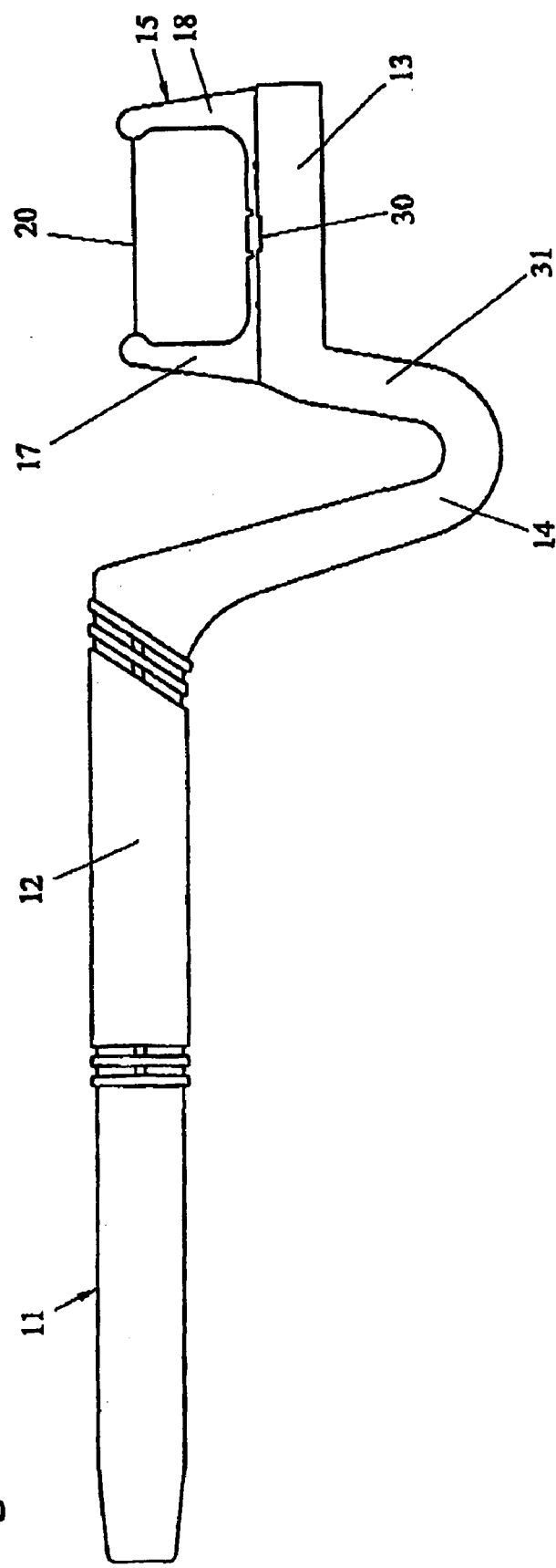
FIG. 1 is a side view of a dental floss holder according to the invention.
Figure 2:
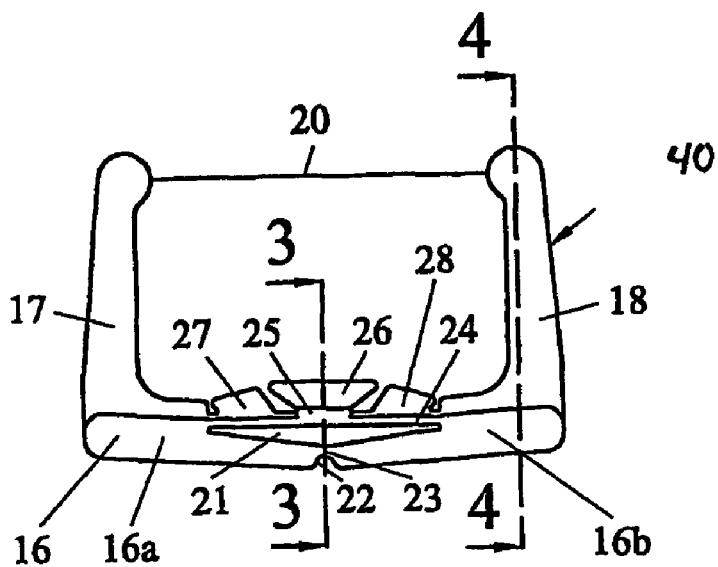
FIG. 2 is a side view of a cartridge with dental floss.

The dental floss holder shown in FIG. 1 has a handle 11 with a handgrip portion 12 and a mounting portion 13 for a cartridge 15. The handle has a bow 14 between the handgrip portion and the mounting portion. The cartridge 15 is shown separate as FIG. 5. FIG. 2 shows an alternative design of the cartridge 15. The handle 11 is the same for the cartridge 40 shown as FIG. 2 as for the cartridge 15 shown in FIG. 5. Like parts have been given like references in the two figures.

Figure 3:
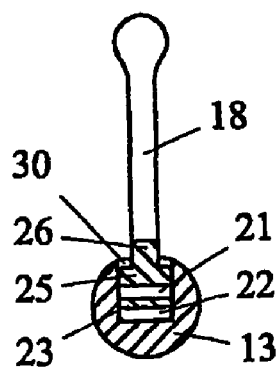
FIGS. 3 and 4 are sections taken along lines 3—3 and 4—4, respectively, in FIG. 2.
Figure 4:
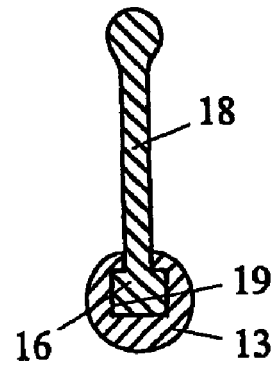

The cartridge 40 shown in FIG. 2 is shown mounted in the handle in the FIGS. 3 and 4. It is U-formed and comprises a base 16 and two legs 17,18. The legs are thinner than the base so that the base can be axially inserted into an axial recess, a keyhole-formed groove 19, in the mounting portion 13 of the handle. The base 16 is thus, the, portion of the cartridge for fastening the cartridge to the handle. A dental floss 20 is mounted between the legs 17,18. The cartridge 40 is suitably injection-moulded in an environmentally harmless, bendable plastics, for example polypropylene or polyethylene, and the dental floss can advantageously be fastened by being moulded into the legs, an economical way of fabrication. The base 16 has a triangular longish transverse slot or recess 21 with a dull angle adjacent a transverse recess 22. The recess 22 forms a weakening of the base 16 and the base forms a bow in that it has two straight portions 16a and 16b that form a dull angle in the weakening 23. The part of the base above the slot 21 is in the form of a thin straight band 24 with a head 25. Since this band 24 is straight, the base 16 will be thicker vertically adjacent the slot 21 than at both sides thereof. On top of the head 25, there is a part 26 with the same width as the legs 17,18 so that it fits in the thin part of the keyhole groove 19. There is an upstanding part 27,28 on each side of the central upstanding part 26. These upstanding parts 27,28 give a torsional stability to the band 24 and the joints between them permit some stretching.

The keyhole groove 19 of the mounting portion 13 of the handle 11 has a locking portion 30 that has the same length as the head 25 and has a uniform width, that is, it has not the keyhole form. The head 25 fits in the locking recess 30 and the mouth of the groove 19 has a non-illustrated chamfer that guides the head 25 into the groove 19. When the base 16 is forced into the groove, the head slides into the groove and snaps out into the recess 30 and locks the cartridge 40 to the handle 11. The thin band or belt 24 will be somewhat stretched in its four joints when the base is straightened and it will hold the head in place by its spring action. The legs 17,18 will be forced apart when the base is straightened so that they are bent and by their spring force they will maintain the dental floss 20 tensioned also if the floss should stretch when becoming wet. The entire cartridge can be economic in the consumption of material since the floss will not be tensioned until the cartridge is mounted. The cartridge can be stored for a long period, and the legs can be comparatively weak since they have to keep the dental floss tensioned for a short period only. The length of the dental floss can for example be about 20 mm and the thickness of the base 16 can for example be about 3 mm. The legs 17,18 are thinner and weaker than the base 16 and they will still provide a great tension in the floss because the design of the mounting of the cartridge will provide for a large bending of the legs. The design of the mounting part 13 of the handle 11 and the cartridge 40 makes it small but strong and therefore convenient to use for cleaning of the teeth and still providing a great tension in the floss. The mounting part 13 of the handle is stronger than the base 16 and will not be bent during the mounting. The mounting part 13 is shown straight and the base 16 bow-formed. It is also possible to have the mounting part bow-formed so that it bends the base 16 instead of straightening it when the cartridge is being mounted.

The head 25 moves down into the groove 19 when one pushes down the part 26 and one can then easily pull the cartridge out of the groove. With this design of the mounting part 13 of the handle 11 and the locking element 25, the teeth can not get in touch with the locking element and therefore not unlock and remove the cartridge 40.

The illustrated bow 14 makes space for the corners of one's mouth when the teeth at the back of the mouth are cleaned. It is directly adjacent the mounting part 13 and designed to make the dental floss 20 aligned with or at least almost aligned with the hand grip 12 of the handle 11. There will therefore be no torque on the handle during cleaning of the teeth. The bow 14 and the dental floss 20 are aligned with the hand grip, which makes it possible to use a convenient method for cleaning of the teeth by holding the handle 11 like a pen and easily turn the handle so that one can easily clean all teeth, also the teeth at the back of the mouth. This method feels natural and improves the cleaning of the teeth. The angle between the part 31 of the bow and the base 16 should preferably be bigger than a right angle, suitably about 10 degrees bigger, and there should be no edge between the parts 31 and 17 that could catch the corner of the mouth, that is, there should be a functionality smooth transition between the parts 17 and 31. A corner or edge that is 1 or 2 mm in size cannot catch the corner of the mouth and would therefore not be detrimental to the function. The depth of the bow 14 from the hand grip 12 is preferably twice the length of the legs 17, 18 or more as illustrated so that the length from the bottom of the bow 14 to the dental floss is about twice the length of the legs or even more. The distance from the bottom of the bow to the centre line of the handgrip 12, that is, the distance to the dental floss, should be at least 22 mm, preferably at least 25 mm. It could advantageously be 30–31 mm. The bow makes space for the corner of the mouth notwithstanding the small height of the cartridge 40, which makes the holder convenient to use. The cartridge is small, thin and flat, which makes a package of a plurality of cartridges small and convenient. Instead of a mounting portion 13 of the handle having a groove 19 in which the base 16 is inserted, the base could be a sleeve-like and pushed onto a rod-like mounting portion of the handle. A disadvantage would be that the cartridge would be somewhat bulkier. It would also be possible to have a cartridge base that could be transversely snapped onto the mounting portion of the handle instead of being axially pushed onto it, but such a design would still be bulkier.

Figure 5:
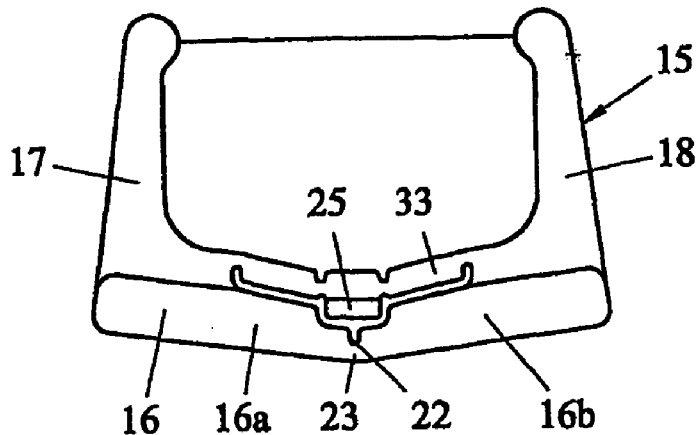
FIG. 5 is a side view of a cartridge also shown in FIG. 1.

FIG. 5 shows the cartridge 15, which is somewhat modified from the one in FIG. 2 and like parts have been given like reference. The head 25 is carried by a thin band 33 that has the same width as the legs 17,18 and that has a bow-form as has the main part of the base 16. The band will be straightened out when the base is inserted into the groove 19 of the handle and it will raise the head 25 into portion 30 of the keyhole 19 and keep the cartridge in place. By pushing down the band 33 with one's thumb, one can release the head from the recess 30 and remove the cartridge 15 from the handle 11 in the same way as in the previously described design. The design of FIG. 5 might be the preferred design.

Figure 6:
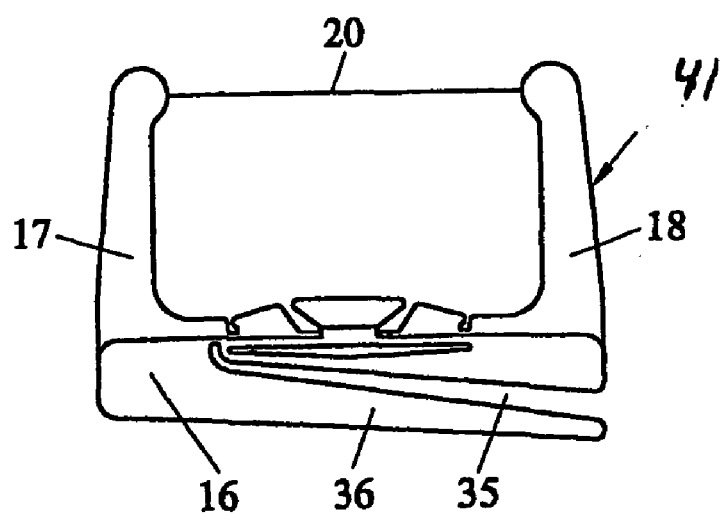
FIG. 6 shows a modified design of the cartridge shown in FIG. 5.

FIG. 6 shows another alternative design 41 of the cartridge 15. Its base 16 is straight but it has a slot 35 that provides a lever 36 that bends the leg 17 and tensions the dental floss 20 when the base is forced into the mounting portion 13 of the handle shown in FIG. 1.

Figure 7:
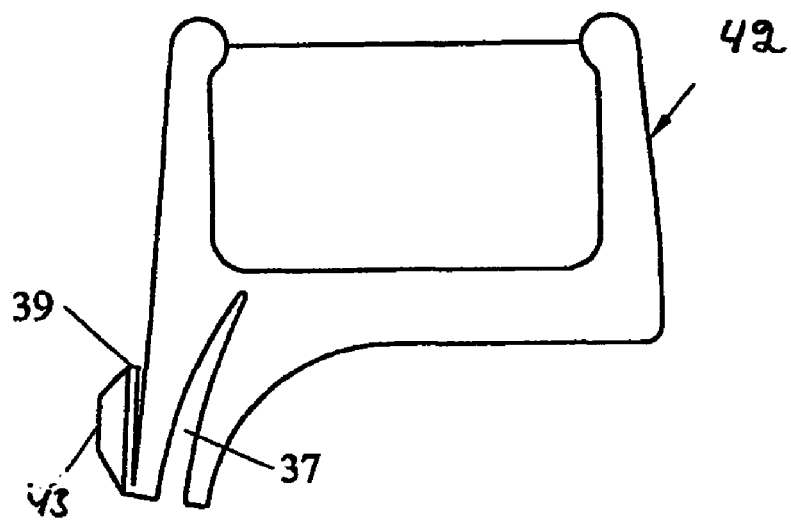
FIG. 7 shows another example of a cartridge with a dental floss.
Figure 8:
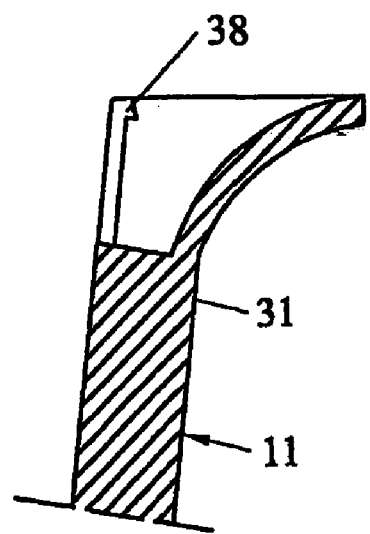
FIG. 8 shows the mounting end of a handle for the cartridge shown in FIG. 7.

FIG. 7 shows an alternative design 42 of both the cartridge 15 and the cartridge-receiving portion of the handle 11. Only the part 31 of the handle 11 is shown that corresponds to the part 31 in FIG. 1 and this part 31 forms also the cartridge-receiving portion of the handle. Also in this design, the dental floss 20 is tensioned when the cartridge is mounted on the handle when a slot 37 is compressed. A snap lock is formed by two rigid parallel hooks 38 that hook into a surface 39. The snap lock is released when one pushes down the part 43 between the hooks 38.

The invention claimed is:

1. A dental floss holder, comprising
    a handle (11),
    a cartridge (15, 40, 41) having a base (16), two legs (17, 18) and dental floss (20) suspended between the two legs (17, 18), and
    a cooperating arrangement situated between a fastening portion on the base (16) of the cartridge (15, 40, 41) and a mounting portion (13) of the handle (11) for receiving the fastening portion and bending the cartridge base (16) in a plane of the legs (17, 18) in response to the fastening portion being mounted to the handle (11), thereby stressing the legs (17, 18) away from each other and tensioning the dental floss (20).

2. A dental floss holder according to claim 1, wherein the base (16) forms said fastening portion and said co-operating means comprises the base (16) and a receiving recess (19) in the mounting portion (13) of the handle into which recess the base (16) can be axially forced, and one of said base and recess is bow-formed in the plane of said legs (17, 18).

3. A dental floss holder according to claim 2, wherein the base (16) is bow-formed and the receiving recess (19) straight.

4. A dental floss holder according to claim 3, wherein the mounting portion (13) of the handle is offset from a handgrip portion (12) of the handle and the dental floss (20) is in the line with the handgrip portion.

5. A dental floss holder according to claim 2, wherein the receiving recess (19) has the form of a keyhole.

6. A dental floss holder according to claim 5, wherein the mounting portion (13) of the handle is offset from a handgrip portion (12) of the handle and the dental floss (20) is in the line with the handgrip portion.

7. A dental floss holder according to claim 2, wherein the mounting portion (13) of the handle is offset from a handgrip portion (12) of the handle and the dental floss (20) is in the line with the handgrip portion.

8. A dental floss holder according to claim 1, wherein the mounting portion (13) of the handle is offset from a handgrip portion (12) of the handle and the dental floss (20) is in line with the handgrip portion.

9. A dental floss holder according to claim 8, wherein the handle (11) has a bow (14) for the corner of the mouth between the hand grip portion (12) and the mounting position (13).

10. A dental floss holder according to claim 9, wherein the bow (14) for the corner of the mouth is in the plane of the legs (17, 18).

11. A dental floss holder according to claim 9, wherein there is a smooth transition between the bow (14) and the cartridge (15).

12. A dental floss holder according to claim 9, wherein the depth of the bow (14) from the hand grip portion (12) is about twice the length of the legs (17, 18) or more.

13. A dental floss holder according to claim 3 wherein the receiving recess (19) has the form of a keyhole.

14. A dental floss holder, comprising
a handle (11),
a cartridge (42) having a base, two legs and dental floss suspended between the two legs, and
a cooperating arrangement situated between a fastening portion (37, 39, 43) on the base of the cartridge (42) and a mounting portion of the handle (11) for receiving the fastening portion (37, 39, 43) and bending the fastening portion (37, 39, 43) in response to the fastening portion being mounted to the handle (11), thereby stressing the legs and tensioning the dental floss.

15. A dental floss holder according to claim 14, wherein the fastening portion (37, 39, 43) comprises two projections extending in a direction from the base away from the dental floss and defining a slot therebetween,
such that when the cartridge (42) is mounted on the handle (11) the defined slot (37) is compressed between the projections and tensions the dental floss.

16. The dental floss holder according to claim 15, wherein the fastening portion (37, 39, 43) additionally comprises a part (43) mounted upon an end of one of the projections away from the dental floss and extending towards the dental floss and in turn having an end surface (39) at an end thereof remote from said one projection, and
the mounting portion of the handle (11) comprises at least one hook (38) situated at a mouth of an opening in the handle (11) for receiving the cartridge (42), such that when the cartridge (42) is inserted into the opening, the at least one hook (38) hooks onto the end surface (39) of the part (43) to create a snap lock.

17. The dental floss holder according to claim 1, wherein the fastening portion on the base (16) comprises a lever (36) projecting therefrom to define a slot (35) therebetween, such that when said fastening portion is inserted into said mounting portion of the handle (11), the lever (36) bends the legs (17, 18) and tensions the dental floss (20).

18. The dental floss holder according to claim 1, wherein the base (16) comprises a slot (21) extending transversely therethrough and having a triangular cross-section with a vertex pointing away from the dental floss (20) and three upstanding projections (26, 27, 28) from the base (16) towards the dental floss (20) and adjacent the slot (21) to provide torsion stability and permit stressing of the legs (17, 18) upon mounting on the handle (11).

* * * * *

UNITED STATES PATENT AND TRADEMARK OFFICE
CERTIFICATE OF CORRECTION

PATENT NO. : 7,146,989 B2
APPLICATION NO. : 10/399348
DATED : December 12, 2006
INVENTOR(S) : Erik Forsell It is certified that error appears in the above-identified patent and that said Letters Patent is hereby corrected as shown below:

On the Title page at item (76) Inventor:

"ERIK FORSSELL" should be --ERIK FORSELL--.

Signed and Sealed this

Seventeenth Day of April, 2007

JON W. DUDAS
*Director of the United States Patent and Trademark Office*